(12) United States Patent
Baiko et al.

(10) Patent No.: US 10,688,265 B2
(45) Date of Patent: Jun. 23, 2020

(54) PATIENT INTERFACE DEVICE HAVING MULTI-CHAMBER ADJUSTABLE CUSHION, AND APPARATUS AND METHOD FOR ADJUSTING SAME

(71) Applicant: KONINKLIJKE PHILIPS N.V., Eindhoven (NL)

(72) Inventors: Robert William Baiko, Pittsburgh, PA (US); Daniel James Miller, Cranberry Township, PA (US); Alicia Marie Zack, Jeannette, PA (US)

(73) Assignee: Koninklijke Philips N.V., Eindhoven (NL)

( * ) Notice: Subject to any disclaimer, the term of this patent is extended or adjusted under 35 U.S.C. 154(b) by 381 days.

(21) Appl. No.: 15/633,794

(22) Filed: Jun. 27, 2017

(65) Prior Publication Data

US 2017/0291002 A1 Oct. 12, 2017

Related U.S. Application Data

(62) Division of application No. 14/384,190, filed as application No. PCT/IB2013/051722 on Mar. 5, 2013, now Pat. No. 9,717,871.
(Continued)

(51) Int. Cl.
*A61M 16/06* (2006.01)
*A61M 16/00* (2006.01)
*A61M 16/20* (2006.01)

(52) U.S. Cl.
CPC .... *A61M 16/0622* (2014.02); *A61M 16/0003* (2014.02); *A61M 16/06* (2013.01);
(Continued)

(58) Field of Classification Search
CPC .......... A61F 13/00055; A61F 13/00063; A61F 13/00068; A61F 13/0203; A61F 13/023;
(Continued)

(56) References Cited

U.S. PATENT DOCUMENTS 5,450,843 A 9/1995 Moll
6,615,832 B1 9/2003 Chen
(Continued)

FOREIGN PATENT DOCUMENTS

EP 2147769 A1 7/2010
WO WO2007068044 A1 6/2007
(Continued)

*Primary Examiner* — Annette Dixon
(74) *Attorney, Agent, or Firm* — Michael W. Haas

(57) ABSTRACT

A cushion member for a patient interface device that includes a main body portion including a plurality of chambers and a self-sealing cap portion coupled to the main body portion. The cap portion covers each of the chambers and forms a plurality of membrane members, with each membrane member being positioned over and sealing a respective one of the chambers. The cap portion is made of a self-sealing material such that that each of the membrane members is structured to self-seal responsive to having a needle inserted through and pulled out of the membrane member. Also, an apparatus and a method for selectively adjusting the internal pressure of the chambers of such a cushion.

19 Claims, 12 Drawing Sheets

Related U.S. Application Data

(60) Provisional application No. 61/610,014, filed on Mar. 13, 2012.

(52) U.S. Cl.
CPC .... A61M 16/0616 (2014.02); A61M 16/0633 (2014.02); A61M 16/0644 (2014.02); A61M 16/0694 (2014.02); A61M 16/20 (2013.01); A61M 2016/0027 (2013.01); A61M 2016/0661 (2013.01); A61M 2205/3331 (2013.01); A61M 2207/00 (2013.01); A61M 2209/04 (2013.01); A61M 2209/045 (2013.01)

(58) Field of Classification Search
CPC .. A61F 2013/00174; A61F 2013/00182; A61F 2013/00553; A61F 2013/0057; A61F 2013/00846; A61F 2013/0091; A61F 2013/00927; A61F 2013/00944; A61F 2013/00957; A61M 1/0027; A61M 1/0031; A61M 1/0088; A61M 1/009; A61M 16/0051; A61M 16/024; A61M 16/06; A61M 16/0605; A61M 16/0633; A61M 16/0638; A61M 16/0644; A61M 16/0655; A61M 16/0694; A61M 2016/0661; A61M 2205/15; A61M 2205/3344; A61M 2205/3368; A61M 2205/3375; A61M 2205/3584; A61M 2205/3592; A61M 2205/502; A61M 2205/52; A61M 2205/581; A61M 2205/583; A61M 2205/6018; A61M 2205/702; A61M 2205/8206; A61M 27/00
See application file for complete search history.

(56) References Cited

U.S. PATENT DOCUMENTS

| | | | |
|---|---|---|---|
| 6,834,650 B1 * | 12/2004 | Fini | A61M 16/06 128/205.25 |
| 7,278,428 B2 * | 10/2007 | Fini | A61M 16/06 128/205.25 |
| 7,665,464 B2 | 2/2010 | Kopacko | |
| 8,276,588 B1 | 10/2012 | Connor | |
| 8,372,507 B1 | 2/2013 | Gess | |
| 8,789,532 B2 * | 7/2014 | Hansen | A61M 16/06 128/206.21 |
| 2005/0072428 A1 * | 4/2005 | Ho | A61M 16/06 128/205.25 |
| 2005/0205096 A1 | 9/2005 | Matula, Jr. | |
| 2007/0078366 A1 * | 4/2007 | Haggstrom | A61F 13/0203 602/53 |
| 2009/0014007 A1 | 1/2009 | Brambilla | |
| 2010/0024811 A1 | 2/2010 | Henry | |
| 2010/0199992 A1 | 8/2010 | Ho | |
| 2011/0153017 A1 | 6/2011 | McClellan | |
| 2011/0220112 A1 | 9/2011 | Connor | |
| 2012/0240933 A1 * | 9/2012 | Haas | A61M 16/06 128/204.21 |
| 2012/0316645 A1 | 12/2012 | Grotz | |

FOREIGN PATENT DOCUMENTS

| | | |
|---|---|---|
| WO | WO2009062265 A1 | 5/2009 |
| WO | WO2009143586 A1 | 12/2009 |

\* cited by examiner

PATIENT INTERFACE DEVICE HAVING MULTI-CHAMBER ADJUSTABLE CUSHION, AND APPARATUS AND METHOD FOR ADJUSTING SAME

CROSS-REFERENCE TO RELATED APPLICATIONS

This patent application is a Divisional under 35 U.S.C. § 120 of U.S. patent application Ser. No. 14/384,190, filed Sep. 10, 2014, which claims the priority benefit under 35 U.S.C. § 119(e) of U.S. Provisional Application No. 61/610,014 filed on Mar. 13, 2012, the contents of which are herein incorporated by reference.

BACKGROUND OF THE INVENTION

1. Field of the Invention

The present invention relates to patient interface devices for transporting a gas to and/or from an airway of a user, and in particular, to a patient interface device that includes a cushion member having multiple chambers in which the internal pressure of the chambers may be selectively and individually adjusted. The present invention also relates to an apparatus and method for selectively and individually adjusting the chambers within such a cushion member.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA).

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the patient's nose and mouth, a full face mask that covers the patient's face, or a total face mask that covers the entirely of the patient's face including the eyes and forehead. The patient interface device interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

As is known, proper patient interface device fit is important, as a poor fit can lead to patient discomfort and/or problems with mask stability and/or mask to patient seal. One of the problems with current patient interface devices is that they are typically made with the idea that a particular device style/design or a certain number of sizes of a particular device style/design will be able to accommodate the entire population of patients. This, however, is not the case because facial geometries can vary greatly from person to person.

SUMMARY OF THE INVENTION

Accordingly, it is an object of the present invention to provide a cushion member for a patient interface device that overcomes the shortcomings of conventional patient interface devices. This object is achieved according to one embodiment of the present invention by providing a patient interface device that includes a cushion member having multiple chambers wherein the internal pressure of the chambers may be selectively adjusted.

It is yet another object of the present invention to provide an apparatus that enables the internal pressure of the chambers of such a cushion member to be selectively adjusted.

It is yet another object of the present invention to provide a method of adjusting the internal pressure of the chambers of such a cushion member that enables the shortcomings of conventional patient interface devices to be overcome.

In one embodiment, a cushion member for a patient interface device is provided that includes a main body portion including a plurality of chambers and a self-sealing cap portion coupled to the main body portion. The cap portion covers (i.e., extends over) each of the chambers and forms a plurality of membrane members, with each membrane member being positioned over and directly or indirectly sealing a respective one of the chambers. The cap portion is made of a self-sealing material such that that each of the membrane members is structured to self-seal responsive to having a needle inserted through and pulled out of the membrane member.

In another embodiment, a patient interface device adjustment apparatus is provided that includes a cushion support assembly having a plurality of fluid delivery needles extending therefrom, the cushion support assembly being structured to hold a cushion member having a plurality of chambers, each of the chambers being covered and directly or indirectly sealed by a self-sealing membrane member. When the cushion member is held by the cushion support assembly, each fluid delivery needle will be inserted through a respective one of the membrane members and into the chamber that the one of the membrane members covers. The apparatus also includes a fluid delivery module structured to selectively (i) deliver fluid to any one of the chambers through the fluid delivery needle that is inserted into the one of the chambers when the cushion member is held by the cushion support assembly, and (ii) cause fluid present within any one of the chambers to be leaked out of the one of the chambers through the fluid delivery needle that is inserted into the one of the chambers when the cushion member is held by the cushion support assembly.

In still another embodiment, a method of adjusting a cushion member having a plurality of chambers is provided, wherein each of the chambers is covered and directly or indirectly sealed by a self-sealing membrane member. The method includes holding the cushion member in a manner that provides access to each of the chambers through the self-sealing membrane member covering the chamber, and adjusting an internal pressure within each of the chambers through the self-sealing membrane member covering the chamber when the cushion member is engaged by a face of a user.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
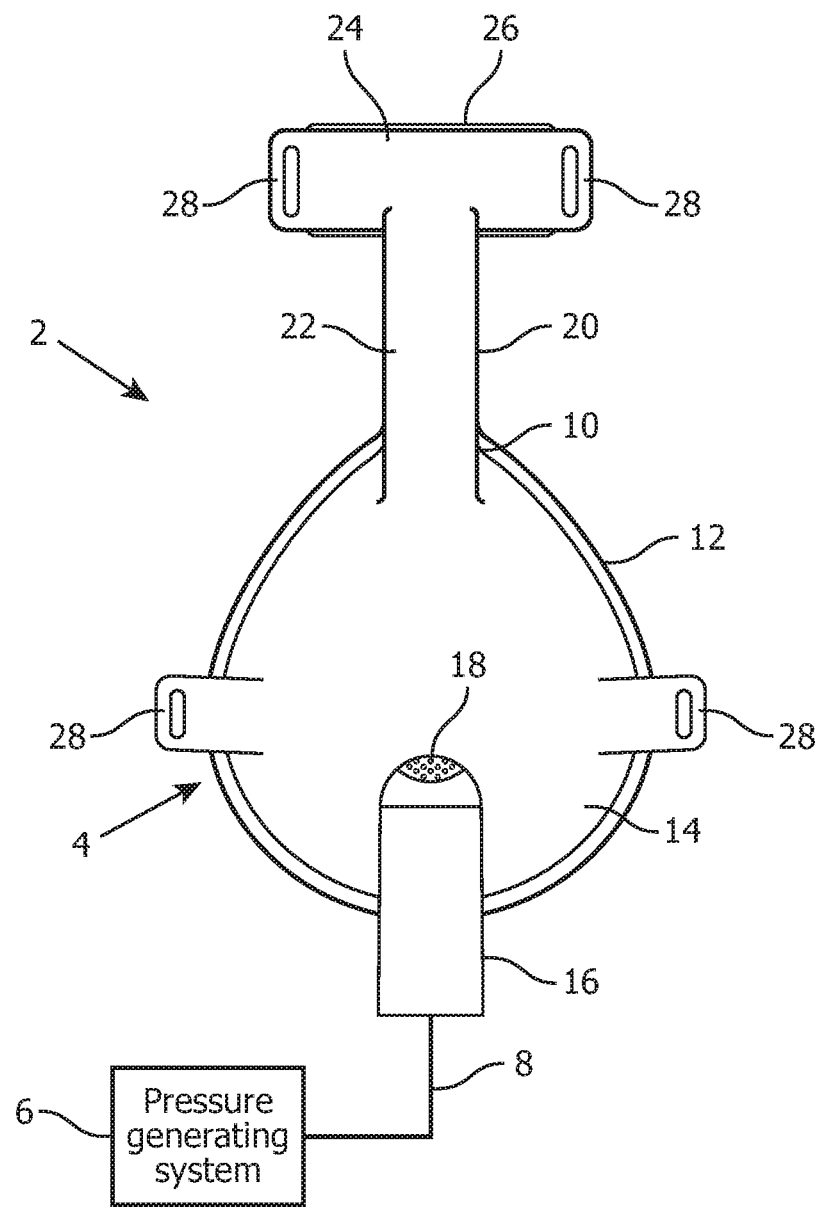
FIGS. 1 and 2 are front and side elevational views, respectively, of a system adapted to provide a regimen of respiratory therapy to a patient according to one exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2:
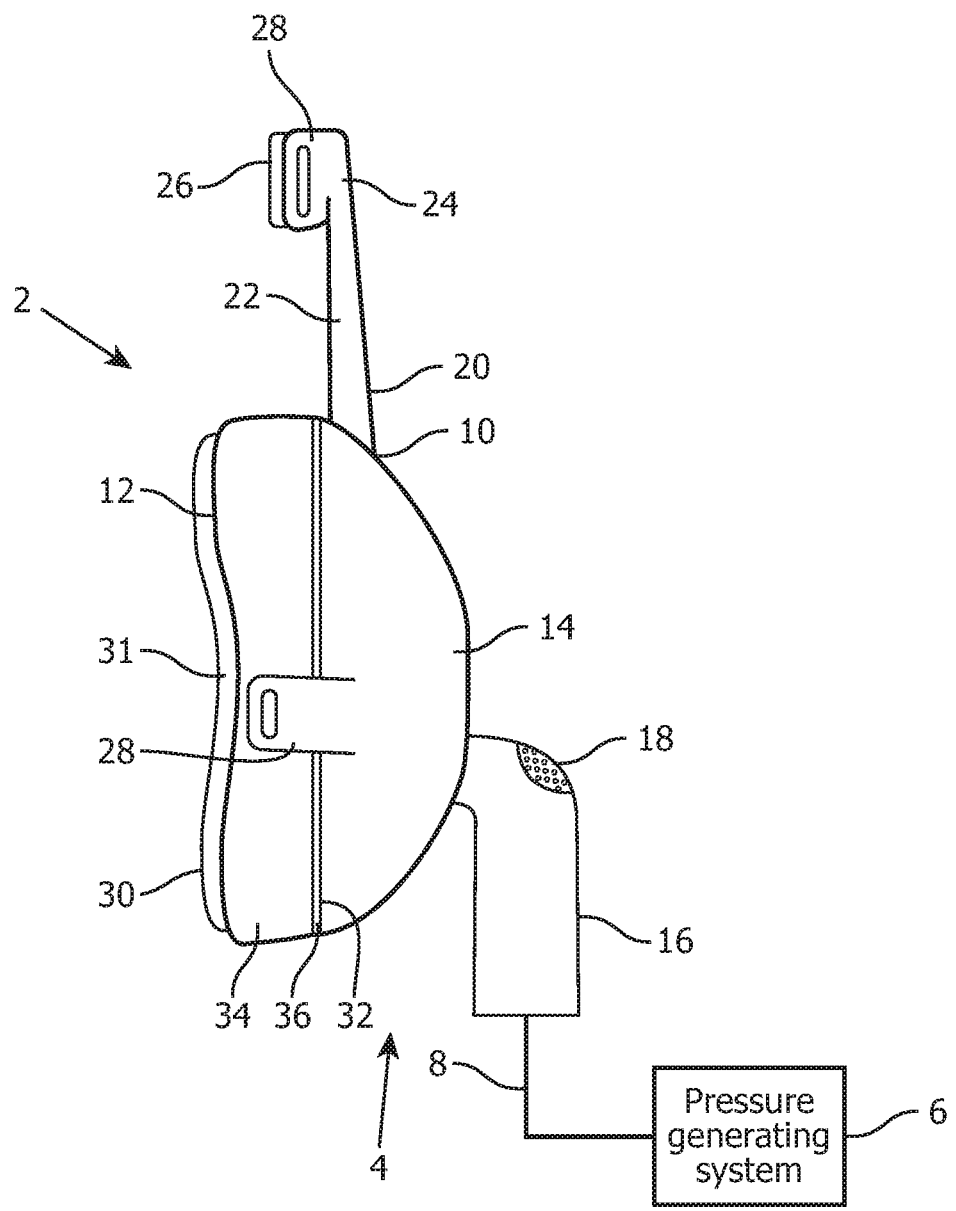

FIGS. 1 and 2 are front and side elevational views, respectively, of a system 2 adapted to provide a regimen of respiratory therapy to a patient according to one exemplary embodiment. As seen in FIGS. 1 and 2, system 2 includes a patient interface device 4 according to one exemplary embodiment that is shown schematically attached to a pressure generating system 6 via a user circuit 8, as is conventionally known in the art. Pressure generating system 6 is any device capable of generating a flow of breathing gas or providing gas at an elevated pressure. Examples of such pressure generating systems include ventilators, constant pressure support devices (such as a continuous positive airway pressure device, or CPAP device) in which the pressure provided to the user is constant over the user's respiratory cycle, and variable pressure devices (e.g., BiPAP®, Bi-Flex®, or C-Flex™ devices manufactured and distributed by Philips Respironics of Murrysville, Pa.) in which the pressure provided to the user varies with the user's respiratory cycle, and auto-titration pressure support devices.

As seen in FIGS. 1-2, patient interface device 4 includes a frame assembly 10 and a cushion member 12 (described in greater detail herein) attached to frame assembly 10. Frame assembly 10 includes a faceplate portion 14. User circuit 8 is coupled to a port defined in faceplate portion 14, and, in the illustrated embodiment, includes an elbow connector 16 for that purpose. In the exemplary embodiment, user circuit 8 is connected to faceplate portion 14 so as to pivot or rotate relative to faceplate portion 14 and may or may not be detachable therefrom. In short, any suitable coupling technique for joining user circuit 8 to faceplate portion 14 is contemplated by the present invention.

In the illustrated exemplary embodiment, an exhaust vent 18 is provided in elbow connector 16 for exhausting a flow of gas from patient interface device 4 to ambient atmosphere. Such exhaust vents are conventionally used in pressure support systems that use a single-limb, i.e., a single conduit, to communicate a flow of gas to an airway of a user. Thus, the present invention contemplates that exhaust vent 18 can be any suitable exhaust vent, and can be located not only on elbow connector 16, but alternatively on another part of patient interface device 4, such as on frame assembly 10.

Patient interface device 4 can have any one of a number of different configurations, shapes, and sizes. In the illustrated, exemplary embodiment, patient interface device 4 is a nasal/oral mask structured to cover the nose and mouth of the patient. However, other types of patient interface devices, such as, without limitation, a nasal mask, a nasal cushion or a full face mask, which facilitate the delivery of the flow of breathing gas to the airway of a patient, may be substituted for patient interface device 4 while remaining within the scope of the present invention.

Frame assembly 10, in the exemplary embodiment, is formed from a rigid or semi-rigid material, such as a polycarbonate or an injection molded thermoplastic. In addition, as seen in FIGS. 1 and 2, frame assembly 10 includes a forehead support 20. The forehead support 20 is generally T-shaped and includes a support arm 22 which is coupled to a forehead support bracket 24. Forehead support bracket 24 includes a forehead pad 26 disposed on the user contacting side to engage the forehead of the user. It is to be understood that the present invention contemplates that forehead support 20, and its individual components, can have any one of a variety of alternative configurations. The present invention also contemplates that forehead support 20 can be eliminated entirely.

In the illustrated, exemplary embodiment, a headgear (not shown) attaches to patient interface device 4 via headgear clips 28. Headgear clips 28 attach to straps (not shown) of the headgear, for example by inserting the straps into slots provided in headgear clips 28. In the illustrated embodiment, headgear clips 28 are attached to each side of forehead support bracket 24 and to each side of the lower portion of frame assembly 10.

Cushion member 12, described in greater detail below, includes a first end portion 30 (defining an orifice) structured to sealingly engage the patient's face (in the illustrated embodiment, first end portion 30 includes a flexible sealing flap 31, which may be omitted in alternative embodiments), and a second end portion 32 (defining an orifice) opposite first end portion 30 that couples to the rear of faceplate portion 14. It is to be understood that the present invention contemplates using any suitable technique for coupling second end portion 32 of cushion member 12 to frame assembly 10. Such techniques may include permanently bonding cushion member 12 to frame assembly 10, for example using adhesives, or attaching cushion member 12 to frame assembly 10 using mechanical fasteners in a manner wherein cushion member 12 is selectively detachable from frame assembly 10. In the illustrated embodiment, faceplate portion 14 and cushion member 12 are generally triangular-shaped and thus each includes an apex region, a bottom region opposite the apex region, and first and second opposite side regions. When coupled to frame assembly 10, an internal chamber defined by cushion member 12 receives the nose and mouth of the user when patient interface device 4 is donned by the user so that the user's airway is in fluid communication with the internal chamber.

Figure 3:
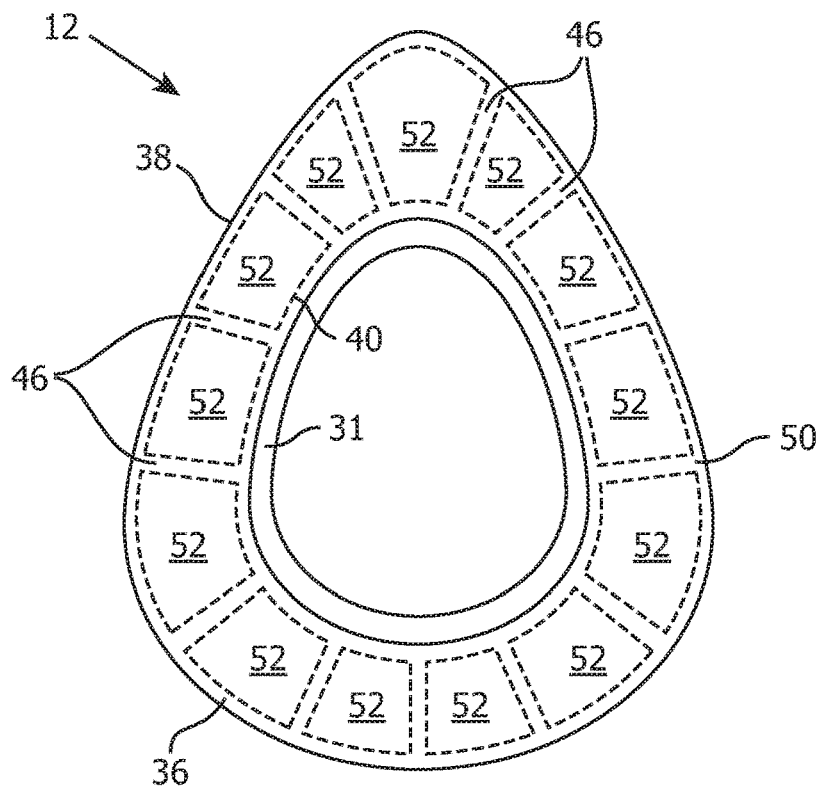
FIG. 3 is a top plan view and FIG. 4 is a side elevational view of a cushion member of a patient interface device of the system of FIGS. 1 and 2 according to an exemplary embodiment of the present invention.
Figure 4:
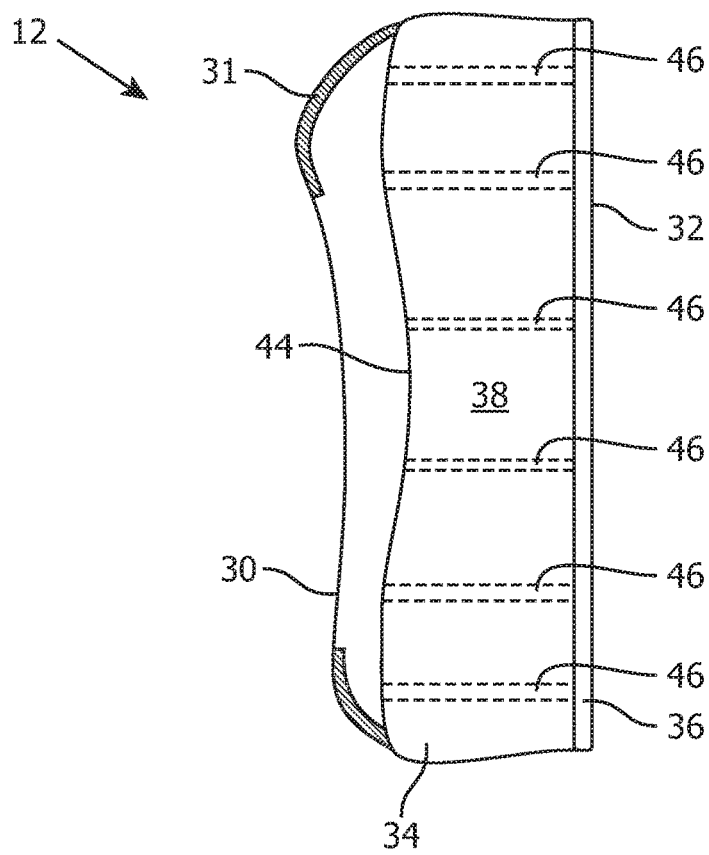

FIG. 3 is a top plan view and FIG. 4 is a side elevational view of cushion member 12 according to an exemplary embodiment of the present invention. As seen in FIGS. 3 and 4, cushion member 12 includes a main body portion 34 and a self-sealing cap portion 36 coupled to main body portion 34, each of which is described in detail below.

Figure 5:
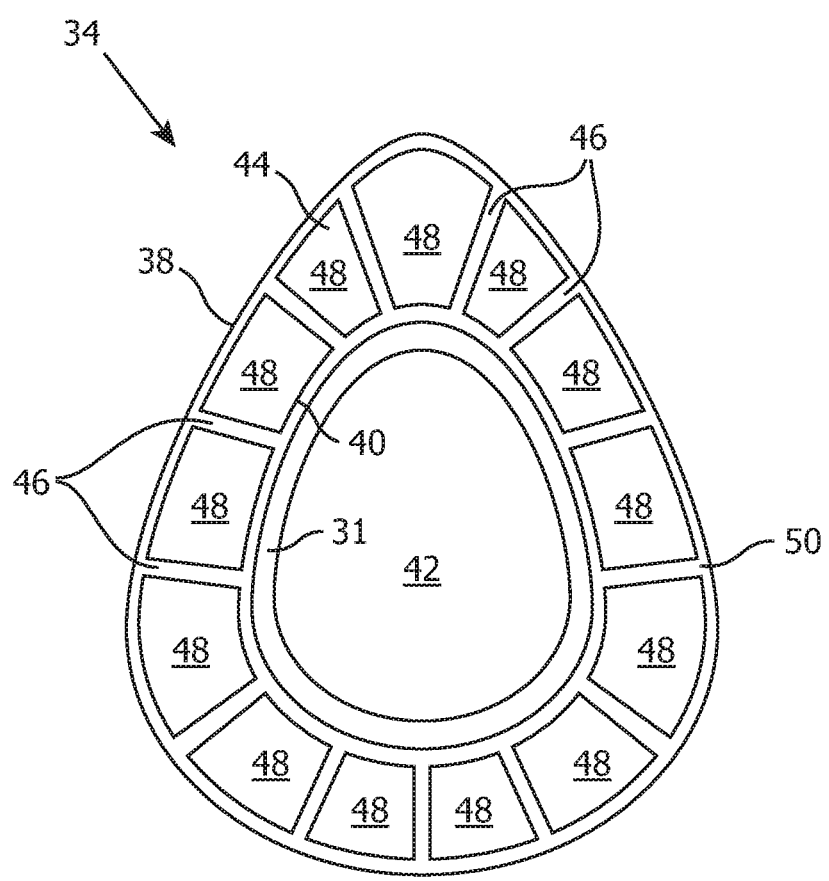
FIG. 5 is a top plan view of the main body portion of the cushion member of FIGS. 3 and 4.

FIG. 5 is a top plan view of main body portion 34. In the exemplary, non-limiting embodiment, main body portion 34 is a unitary structure made (e.g., by a molding process) of a soft, flexible, cushiony, elastomeric material, such as, without limitation, silicone, an appropriately soft thermoplastic elastomer, or any combination of such materials. Main body portion 34 includes an outer wall 38, an inner wall 40 defining an internal chamber 42, and a bottom wall 44 that is coupled to the bottom edges of outer wall 38 and inner wall 40. In the exemplary embodiment, bottom wall 44 has a curved shape such that in cross-section, bottom wall 44, outer wall 38 and inner wall 40 have a U-shape. Main body portion 34 further includes a number of fin members 46 that are spaced about main body portion 34. As seen in FIGS. 3-5, each fin member 46 extends from outer wall 38 to inner wall 40 such that each adjacent pair of fin members 46 form a chamber 48 in main body portion 34. In other words, main body portion 34 includes a plurality of chambers 48 wherein each chamber 48 is defined by outer wall 38, inner wall 40, bottom wall 44 and two immediate adjacent fin members 46 acting as walls. In addition, the top edges of outer wall 38, inner wall 40 and each of the fin members 46 form a top edge 50 of main body portion 34.

Referring again to FIGS. 3 and 4, self-sealing cap portion 36 is attached to top edge 50 of main body portion 34 and, as a result, covers and seals each chamber 48. In the exemplary embodiment, self-sealing cap portion 36 is attached to top edge 50 of main body portion 34 in a secondary molding process wherein the material of self-sealing cap portion 36 is molded onto main body portion 34. In the molding process, this secondary molding is done with main body portion 34 in an upside down position in order to keep the structure of main body portion intact. Thus, self-sealing cap portion 36 forms an individual membrane member 52 over each chamber 48 that seals the chamber 48. Self-sealing cap portion 36 is made of a material that self-seals after being punctured with a needle or similar device, and may be made of, for example and without limitation, room temperature vulcanizing silicone (RTV), liquid silicone rubber (LSR), thermoplastic elastomer (TPE) or some other suitable, self-sealing elastomer material. Thus, as a result of self-sealing cap portion 36 being attached to top edge 50 of main body portion 34, each membrane member 52 forms a self-sealing membrane over the associated chamber 48 such that access to the otherwise airtight chamber 48 may be provided by a needle, after which and chamber 48 will be self-sealed when the needle is removed. The significance of this feature in the context of the present invention is described in greater detail below.

In particular, according to an aspect of the present invention, cushion member 12 is structured to enable the rigidity of different portions of cushion member 12 to be selectively controlled in order to provide for a custom fit for the user of cushion member 12. In particular, each of the chambers 48 of cushion member 12 is structured to allow fluid to be selectively and individually added thereto and removed therefrom such that each chamber 48 can be set to have a desired internal pressure. As used herein, the term "fluid" shall mean a substance, such as, without limitation, liquid, gas or an amorphous solid like a gel, which continually flows/deforms under an applied shear force/stress. For illustrative purposes, the present invention will be described in an implementation wherein the particular fluid used is compressed gas. It will be understood, however, that that is meant to be exemplary only, and that other fluids may also be used within the scope of the present invention. Thus, the gas delivery needles and gas delivery module that are describe herein in connection with the exemplary embodiment may be replaced by some other type of fluid delivery needle/module, such as liquidly delivery needles and a liquid delivery module.

As noted above, in the exemplary embodiment, each of the chambers 48 of cushion member 12 is structured to allow compressed gas (e.g., air) to be selectively and individually added thereto and removed therefrom such that each chamber 48 can be set to have a desired internal gas pressure. The internal gas pressure of each chamber 48 will determine the rigidity of that portion and thus the fit of that portion of cushion member 12 when it is affixed to frame assembly 10 to form patient interface device 4. More specifically, as described in detail herein, the internal gas pressure of each chamber 48 may be set such that a predetermined "target engaged pressure" within each chamber 48 will be achieved when the cushion member is in a condition wherein it engages the patient's face (i.e., when patient interface device 4 is donned by the patient). As will be appreciated, this will mean that each chamber 48 will also then have a corresponding "disengaged pressure" when the cushion member is in a condition wherein it is not in engagement the patient's face (i.e., when patient interface device 4 is not donned by the patient).

Figure 6:
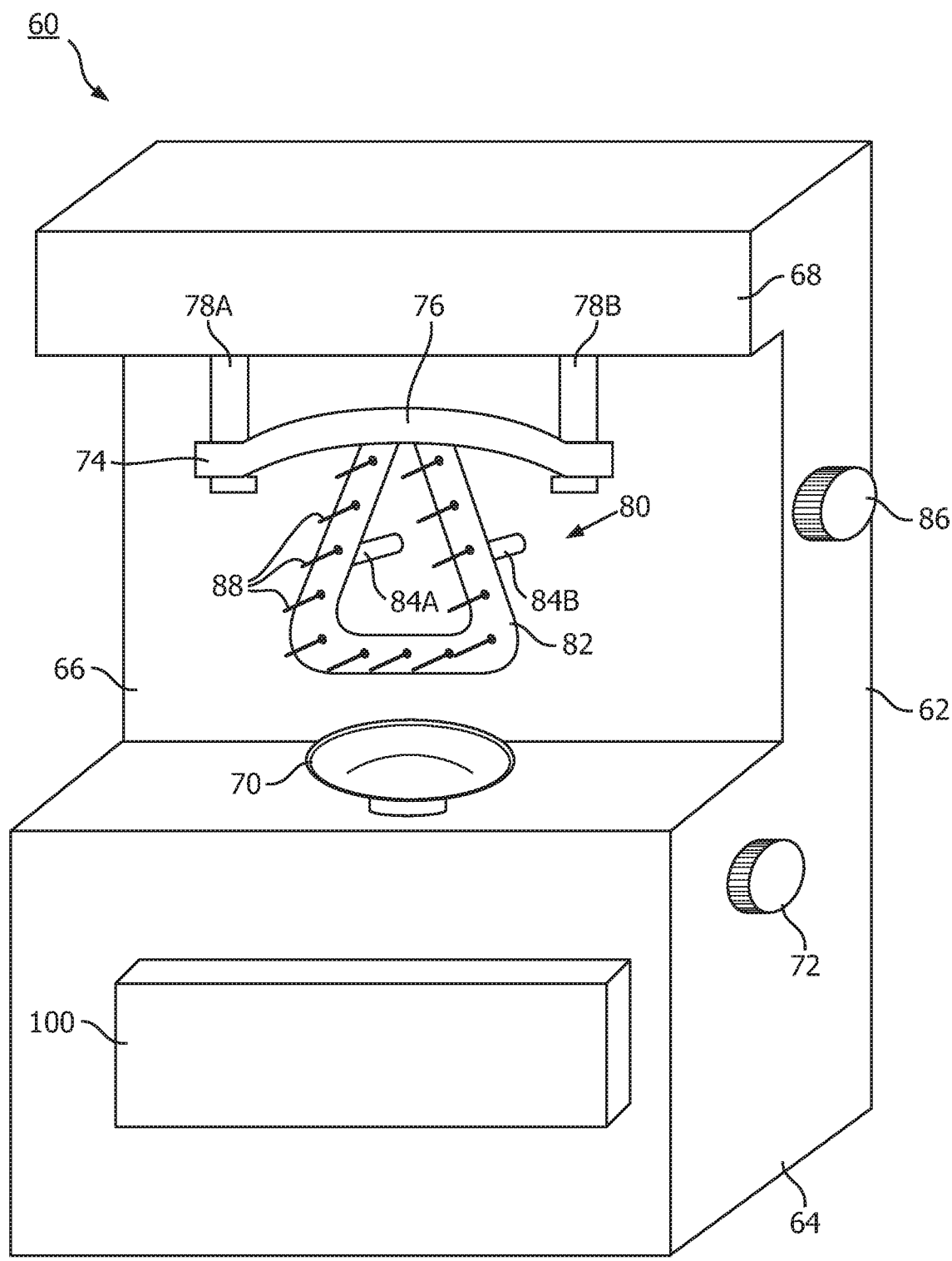
FIG. 6 is a front isometric view of a cushion pressure adjusting apparatus that may be employed to selectively and individually add and remove compressed gas (e.g., air) from each of the chambers of the cushion member of FIGS. 3 and 4 according to one exemplary embodiment.
Figure 7:
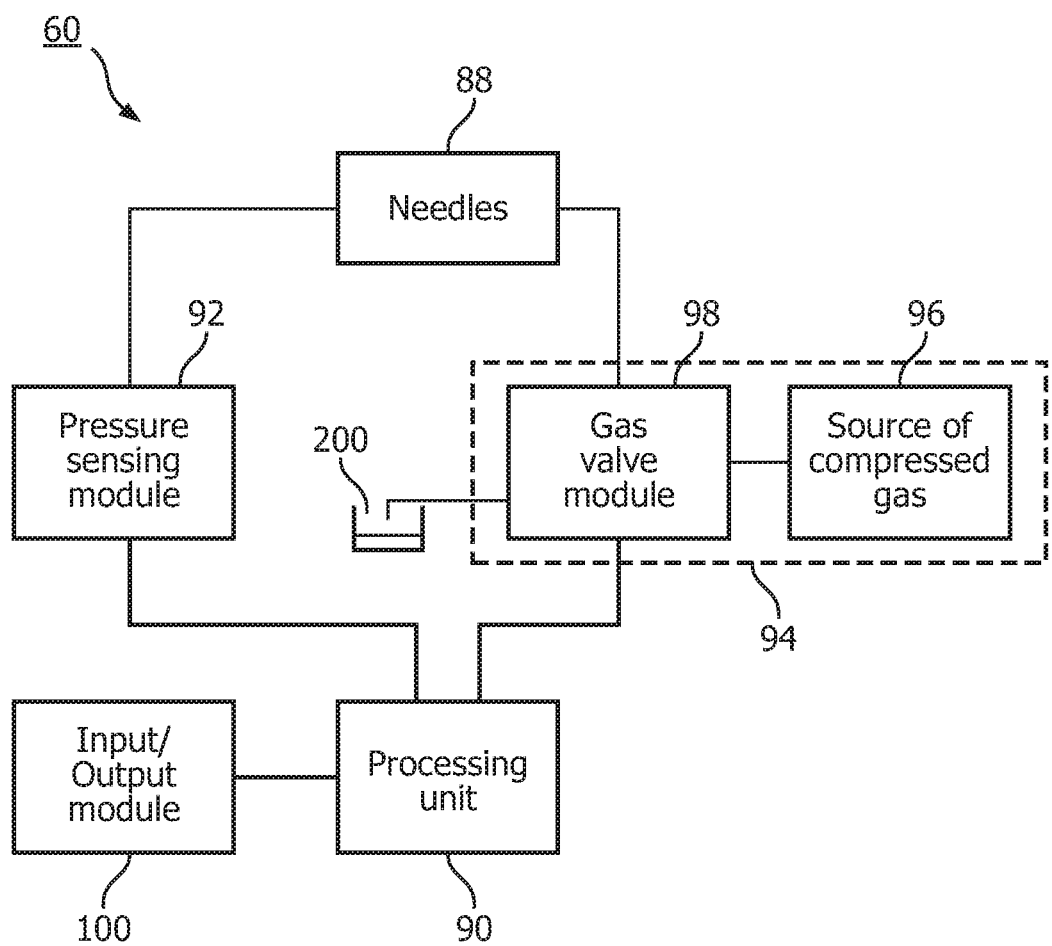
FIG. 7 is a schematic block diagram showing certain selected components of the cushion pressure adjusting apparatus of FIG. 6.

FIG. 6 is a front isometric view of a cushion pressure adjusting apparatus 60 that may be employed to selectively and individually add and remove compressed gas (e.g., air) from each of the chambers 48 of cushion member 12 according to one exemplary embodiment. In addition, FIG. 7 is a schematic block diagram showing certain selected components of cushion pressure adjusting apparatus 60. Cushion pressure adjusting apparatus 60 may be located in any of number of different places, such as, without limitation, in a doctor's office, in durable medical equipment (DME) supplier's office, in a respiratory therapist's office, or even in a retail location, such as a pharmacy, wherein cushion members 12 may be sold.

As seen in FIG. 6, cushion pressure adjusting apparatus 60 includes a main housing 62 having a base portion 64, a middle portion 66 and a top portion 68. Base portion 64 includes a chin rest 70 that extends upwardly therefrom into a space defined in middle portion 66. The height of chin rest 70 relative to base portion 64 is selectively and manually adjustable in a known manner by way of actuator knob 72 that is provided on base portion 64. Alternatively, the height of chin rest 70 relative to base portion 64 may be automatically adjustable by way of a mechanism such as a motor provided in housing 62. Top portion 68 includes a forehead rest member 74 that extends downwardly therefrom into the space defined in middle portion 66. Forehead rest member 74 includes a forehead pad 76 that is slideably attached to post member 78A, 78B extending from top portion 68 (e.g., by way of a friction fit to other know sliding assembly). Thus, the position of forehead pad 76 relative to top portion 68 is selectively and manually adjustable. Alternatively, the position of forehead pad 76 relative to top portion 68 may be automatically adjustable by way of a mechanism such as a motor provided in housing 62.

Cushion pressure adjusting apparatus 60 also includes a cushion support assembly 80 that is adjustably attached to and extends from middle portion 66. More specifically, cushion support assembly 80 includes a support frame 82 that has generally the same shape (e.g., triangular) as cushion member 12. Support frame 82 is attached to post members 82A and 82B which extend from middle portion 66 and which are coupled to a manual actuation mechanism driven by knob member 86 in a known manner. Thus, cushion support assembly 80 may be selectively moved linearly in a direction that is perpendicular to the top surface/plane of support frame 82 by operation of knob member 86. Alternatively, cushion support assembly 80 may be moved automatically by way of a mechanism such as a motor provided in housing 62. Furthermore, a plurality of gas delivery needles 88 are provided on and extend from the top surface of support frame 82. As described in greater detail below, the gas delivery needles 88 are operatively coupled to both a pressure sensing means and a gas delivery means so that pressurized gas may be selectively delivered to and/or extracted from the chambers 48 of cushion member 12 when the needles 88 are inserted through the respective individual membrane members 52.

Referring to FIG. 7, cushion pressure adjusting apparatus 60 also includes a processing unit 90, which may include a microprocessor, a microcontroller, or any other suitable processor, which is operatively coupled to a suitable memory for storing routines to be executed by processing unit 90. Specifically, the memory, which may be separate from and/or internal to the microprocessor, microcontroller or other suitable processor, stores one or more programs/routines for controlling the operation of cushion pressure adjusting apparatus 60 to enable it to perform the various functions and to implement the methods of operation described in greater detail elsewhere herein.

As shown in FIG. 7, cushion pressure adjusting apparatus 60 further includes a pressure sensing module 92 which is coupled to both gas delivery needles 88 and processing unit 90. Pressure sensing module 92 is structured to enable processing unit 90 to determine the internal pressure within each individual chamber 48 of cushion member 12 when a gas delivery needle 88 is inserted into the chamber 48. In one embodiment, pressure sensing module 92 comprises a plurality of individual pressure sensors, with each individual pressure sensor being associated with a respective one of the gas delivery needles 88 to sense the internal pressure of the chamber 48 into which that needle 88 is inserted. Any suitable pressure sensing device may be employed to implement the individual pressure sensors in this embodiment, such as, without limitation, a known or hereafter developed digital pressure sensor. In another, alternative embodiment, pressure sensing module 92 comprises a single pressure sensor that is coupled to both the processing unit 90 and a valve assembly, wherein the valve assembly is in turn coupled to each of the gas delivery needles 88. The valve assembly is structured such that at any one time only one of the gas delivery needles 88 will be connected to the pressure sensor so that the pressure sensor can measure the internal pressure of the associated chamber 48 (and provide that measured pressure to processing unit 90).

Cushion pressure adjusting apparatus 60 also further includes a gas delivery module 94 which is coupled to both gas delivery needles 88 and processing unit 90. As seen in FIG. 7, gas delivery module 94 includes a source of compressed gas (e.g., air) 96, such as, without limitation, a compressor or a pressurized gas tank, that is coupled to a gas valve assembly 98. Gas valve assembly 98 is coupled to each of the gas delivery needles 88 and is structured such that at any one time only one of the gas delivery needles 88 will be connected to source of compressed gas 98 so that, under control of processing unit 90, compressed gas can either be provided to the associated chamber 48 to raise the internal pressure thereof or leaked from the associated chamber 48 (and vented to atmosphere at 200) to lower the internal pressure thereof.

Finally, cushion pressure adjusting apparatus 60 includes an input/output module 100 that enables information (e.g., control and/or operational information) to be input into processing unit 90 and information (e.g., instructions) to be output from processing unit 100. In one non-limiting exemplary embodiment, input/output module 100 is a touch screen, although it may also comprise any number of different human machine interface (HMI) devices such as a separate display, keyboard/keypad and/or mouse.

Figure 8:
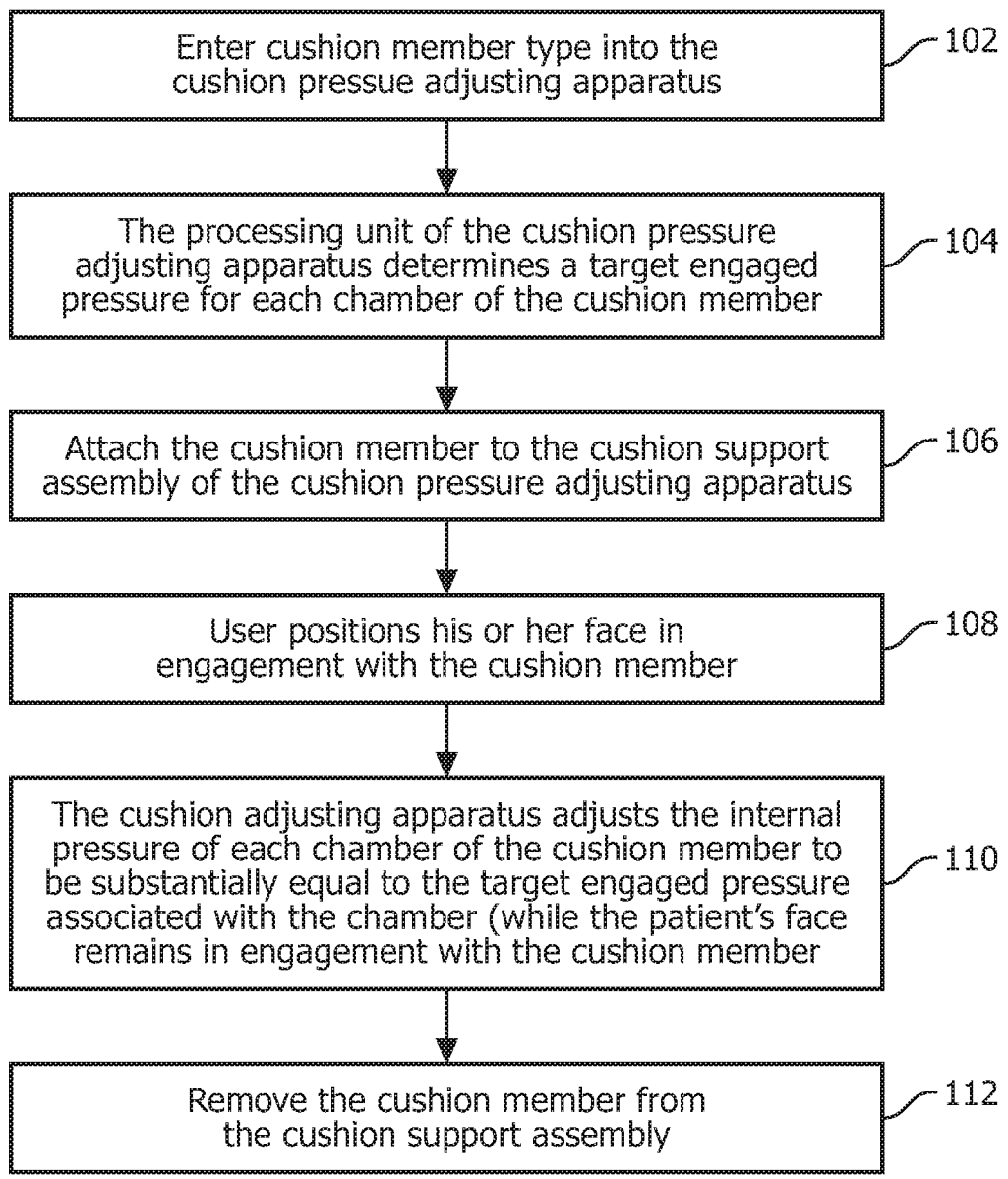
FIG. 8 is a flowchart illustrating a method of custom fitting cushion the member cushion member of FIGS. 3 and 4 according to one exemplary embodiment of the present invention that employs the cushion pressure adjusting apparatus of FIGS. 6 and 7.

FIG. 8 is a flowchart illustrating a method of custom fitting cushion member 12 as described herein according to one exemplary embodiment of the present invention that employs cushion pressure adjusting apparatus 60. The method begins at step 102, wherein the user enters information into cushion pressure adjusting apparatus 60 using input/output module 100 which identifies cushion member 12 by, for example, type, model or the like. In response to receiving such identifying information, processing unit 90 will, at step 104, determine a target engaged pressure for each chamber 48 of cushion member 12. In the exemplary embodiment, processing unit 90 will store such target engaged pressure information for each possible type/model of cushion member 12 that may be employed with cushion pressure adjusting apparatus 60, and will access the appropriate stored information based on the information received in step 102. In each case, the stored target engaged pressure information will identify a specific pressure level for each chamber 48, wherein that pressure level may be the same for each chamber 48 or may vary among the chambers 48. In the exemplary embodiment, those specific pressure levels are chosen in advance (e.g., through testing) as being most suitable for the specific facial contour in question.

Next, at step 106, the user attaches cushion member 12 to cushion support assembly 80. In particular, with second end portion 32 of cushion member 12 facing cushion support assembly 80, cushion member 12 is pushed onto support frame 82 in a manner wherein each gas delivery needle 88 is inserted through a respective membrane member 52 and into a respective chamber 48 of cushion member 12. When this is done, cushion member 12 will be sealingly coupled to cushion support assembly 80 with cushion pressure adjusting apparatus 60 having sealed access to each chamber 48. Then, in step 108, the user positions his or her face in engagement with first end portion 30 of cushion member 12. In particular, the user places his or her chin on chin rest 70 and places his or her forehead against forehead pad 76.

If necessary, the user may adjust chin rest 70 and/or forehead pad 76 as described elsewhere herein so that his or her face will be properly positioned relative to cushion member 12. In the exemplary embodiment, when this is done, first end portion 30 of cushion member 12 will still be spaced from the user' face. Thus, the user then causes cushion support assembly 80 to be moved toward his or her face by turning knob member 86 as described elsewhere herein in order to bring first end portion 30 of cushion member 12 into engagement with his or her face. In the exemplary embodiment, the user moves cushion support assembly 80 until sealing cap portion 36 is spaced about a predetermined distance, such as two inches, from his or her face, as that distance will result in the appropriate level of engagement force between the user's face and main body portion 34 of cushion member 12.

Next, at step 110, while first end portion 30 of cushion member 12 is in engagement with the user's face, cushion pressure adjusting apparatus 60 measures the internal pressure within each chamber 48 using gas delivery needles 88 and pressure sensing module 92 as described herein, and causes the internal pressure within each chamber 48 to be adjusted until it substantially equals the target engaged pressure for that chamber 48 that was determined in step 104 (as used herein "substantially equals" shall mean the actual pressure is within a 10% or less tolerance of the target value). More specifically, under control of processing unit 90, pressurized gas will either be delivered to or leaked from each chamber 48 (sequentially in the exemplary embodiment) using gas valve module 98 and source of compressed gas 96 (if gas is to be added) until the internal pressure within the chamber 48 substantially equals the target engaged pressure for that chamber 48. Then, at step 112, the user detaches cushion member 12 from cushion support assembly 80 by pulling it away from support frame 82. When this is done, each gas delivery needle 88 will be removed from the respective chamber 48 through the respective membrane member 52, after which each membrane member 52 will self-seal as describe herein and maintain the established internal pressure level within the chamber 48.

Thus, as a result of the method steps of FIG. 8, cushion member 12 will be configured such that when it is attached to frame assembly 10 to form patient interface device 4 and thereafter donned by the patent (i.e., the patient's face engages first end portion 30 of cushion member 12), the internal pressure within each chamber 48 will be caused to be at the predetermined target engaged pressure for that chamber 48. As will be appreciated, whenever the patient removes patient interface device 4, the internal pressure within each chamber 48 will return to some disengaged value. However, because the chambers 48 are sealed, any time patient interface device 4 is again donned by the patent, the internal pressure within each chamber 48 will be caused to be return to the predetermined target engaged pressure for that chamber 48.

In an alternative embodiment, following step 106 and prior to step 108, the method includes an additional step wherein cushion pressure adjusting apparatus 60 measures the internal pressure within each chamber 48 using gas delivery needles 88 and pressure sensing module 92 as described herein, and then causes the internal pressure within each chamber 48 to be adjusted until it substantially equals some predetermined initial default pressure value. As a result, when entering step 108, the chambers 48 will all be at substantially the same internal pressure.

Figure 9:
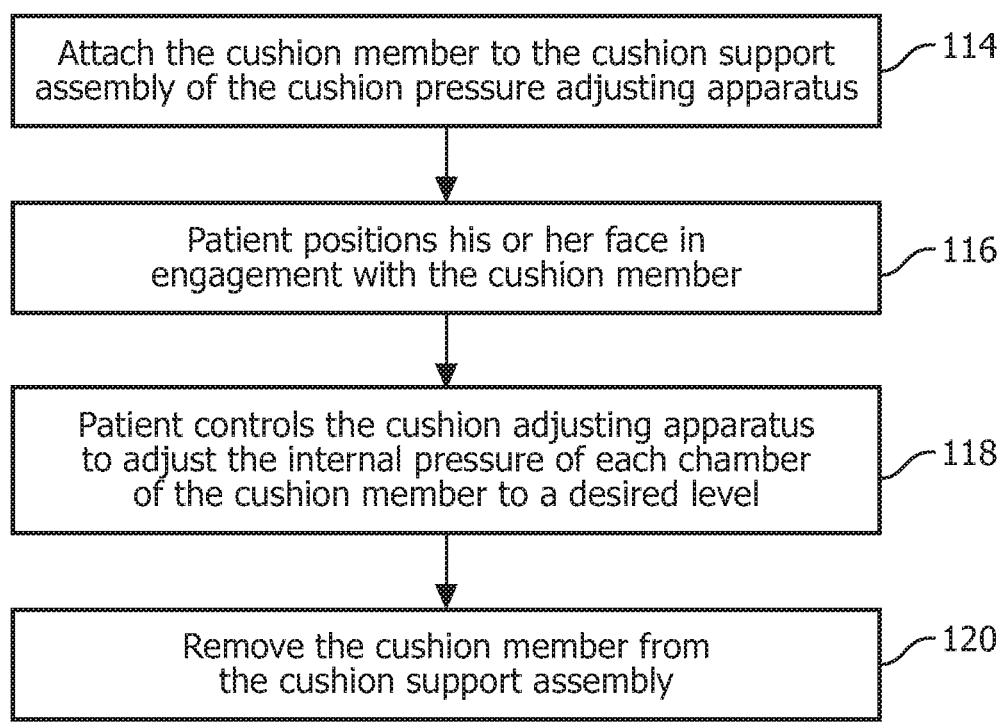
FIG. 9 is a flowchart illustrating a method of custom fitting cushion the member cushion member of FIGS. 3 and 4 according to one exemplary embodiment of the present invention that employs the cushion pressure adjusting apparatus of FIGS. 6 and 7.

FIG. 9 is a flowchart illustrating a method of custom fitting cushion member 12 as described herein according to an alternative exemplary embodiment of the present invention that employs cushion pressure adjusting apparatus 60. The method begins at step 114, wherein the user attaches cushion member 12 to cushion support assembly 80 as described elsewhere herein. Next, in step 116, the user positions his or her face in engagement with first end portion 30 of cushion member 12 as described elsewhere herein. Then, at step 118, while first end portion 30 of cushion member 12 is in engagement with the user's face, the user, by controlling cushion pressure adjusting apparatus 60 through input/output device 100 with appropriate command inputs, causes the internal pressure within each chamber 48 to be selectively adjusted to level that the user finds to be comfortable and desirable.

More specifically, the user, through input/output device 100 and commands provided to processing unit 90, may, as desired, selectively make any chamber 48 "active" and cause pressured gas to be delivered to and/or leaked from the chamber 48 via gas delivery module 94. This process may be repeated until the cushion member 12 as a whole feels comfortable to the user. The end result of step 118 is that each chamber 48 will be at a desired engaged pressure for that chamber 48. Next, at step 120, the user detaches cushion member 12 from cushion support assembly 80 by pulling it away from support frame 82. When this is done, each gas delivery needle 88 will be removed from the respective chamber 48 through the respective membrane member 52, after which each membrane member 52 will self-seal as describe herein and maintain the established internal pressure level within the chamber 48.

Thus, as a result of the method steps of FIG. 9, cushion member 12 will be configured such that when it is attached to frame assembly 10 to form patient interface device 4 and thereafter donned by the patent (i.e., the patient's face engages first end portion 30 of cushion member 12), the internal pressure within each chamber 48 will be caused to be at the desired engaged pressure for that chamber 48 that the user manually set during step 118. As will be appreciated, whenever the patient removes patient interface device 4, the internal pressure within each chamber 48 will return to some disengaged value. However, because the chambers 48 are sealed, any time patient interface device 4 is again donned by the patent, the internal pressure within each chamber 48 will be caused to be return to the desired engaged pressure for that chamber 48 that the user manually set during step 118.

Figure 10:
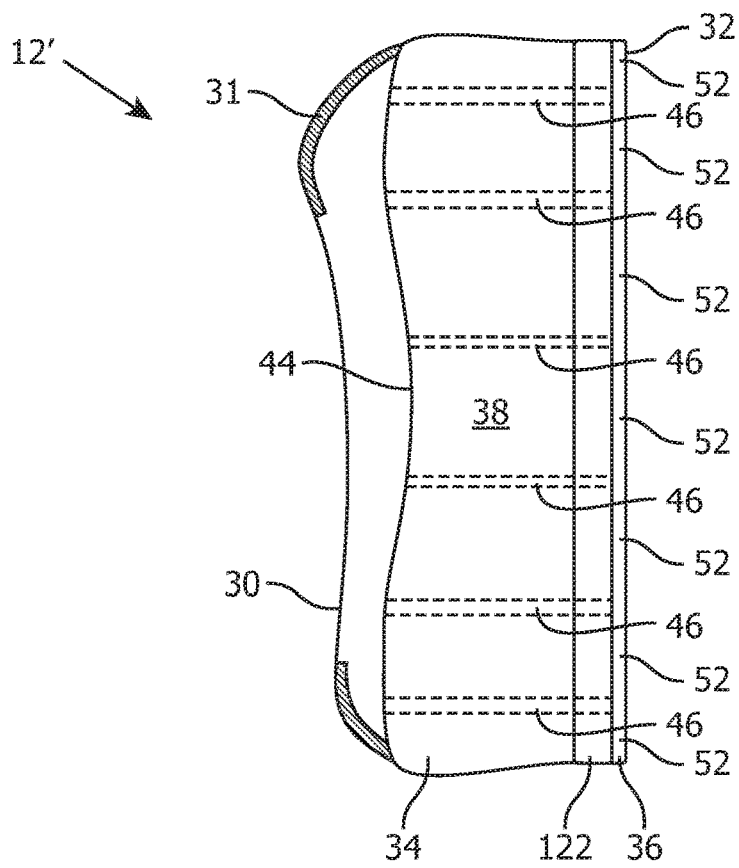
FIG. 10 is a side elevational view of a cushion member according to an alternative exemplary embodiment of the present invention that may be used in the system of FIGS. 1 and 2.

FIG. 10 is a side elevational view of cushion member 12' according to an alternative exemplary embodiment of the present invention. Cushion member 12' may be substituted for cushion member 12 in system 2 and used in connection with cushion pressure adjusting apparatus 60 and the methods of FIGS. 8 and 9. As seen in FIG. 10, cushion member 12' includes a number of the same components as cushion member 12, and like parts are labeled with like reference numerals. In particular, cushion member 12' includes a main body portion 34 as described elsewhere herein (FIG. 5), a frame member 122, and a self-sealing cap portion 36 coupled to frame member 122. Thus, cushion member 12' will include a plurality of chambers 48, with each chamber 48 having an individual membrane member 52 (formed by sealing cap portion 36) over it that seals the chamber 48.

Figure 11:
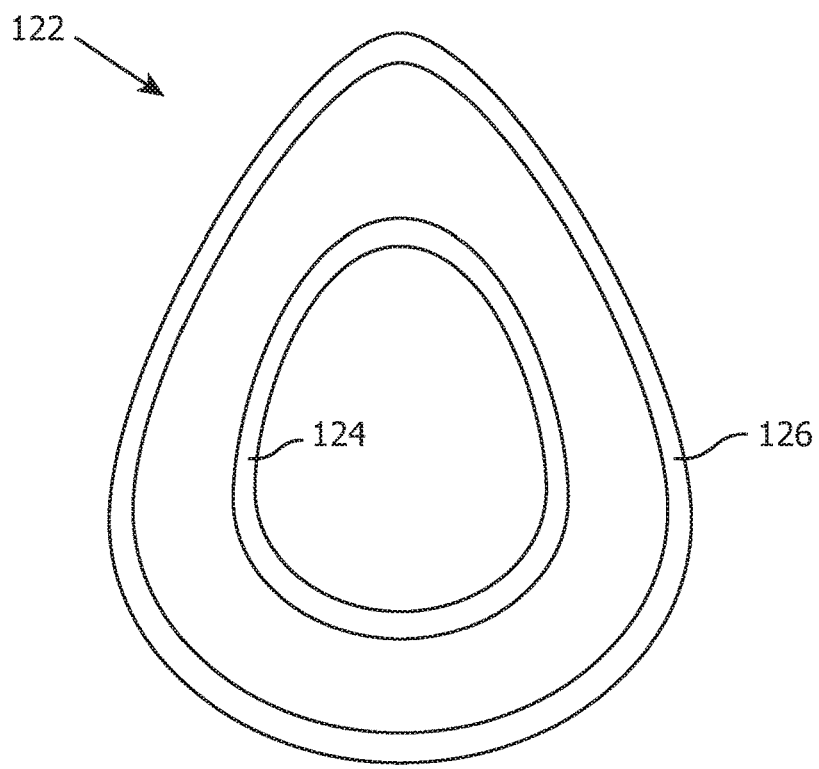
FIG. 11 is a schematic diagram of a frame member of the cushion member of FIG. 10.
Figure 12:
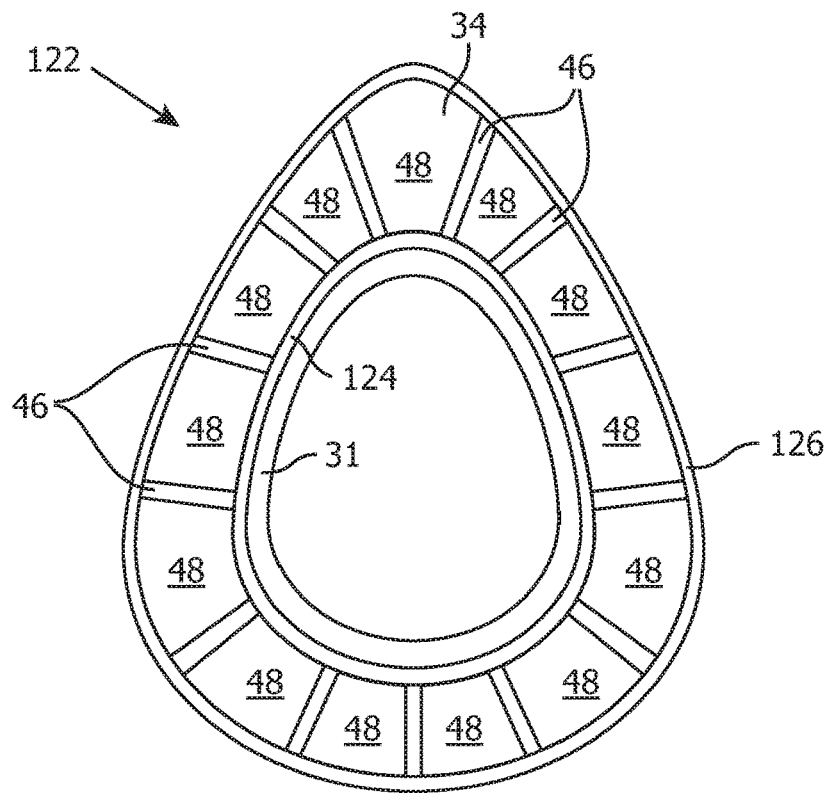
FIG. 12 is a front elevational view and FIG. 13 is a side elevational view of a structure resulting from a cushion main body portion being overmolded on to the frame member of FIG. 11.
Figure 13:
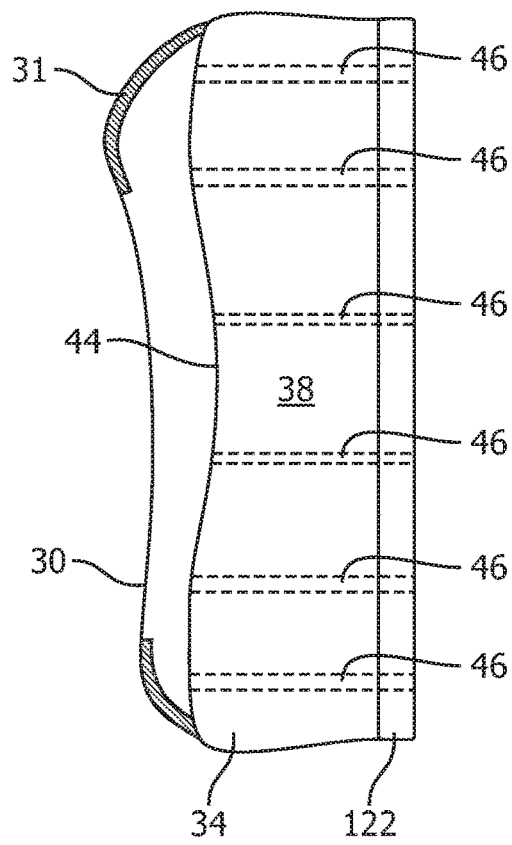

In the exemplary embodiment, cushion member 12' is made by first providing frame member 122 as shown in FIG. 11. Frame member 122 includes inner member 124 and outer member 126, each of which is, in the exemplary embodiment, made of a rigid or semi-rigid material like polycarbonate or an injection molded thermoplastic. Frame member 122 is then inserted in a mold, and main body portion 34 including fin members 46 is overmolded on to a first side of frame member 122, with the result being the structure as shown in FIGS. 12 and 13. Self-sealing cap portion 36 is then overmolded on to a second, opposite side of frame member 122, thereby forming an individual membrane member 52 over each chamber 48.

Figure 14:
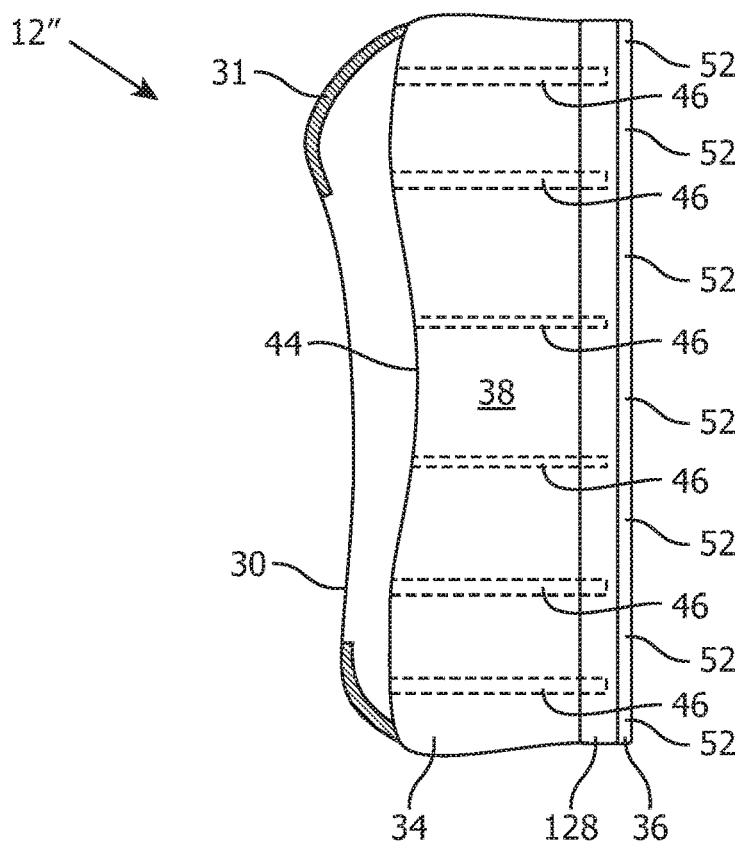
FIG. 14 is a side elevational view of a cushion member according to another alternative exemplary embodiment of the present invention that may be used in the system of FIGS. 1 and 2.

FIG. 14 is a side elevational view of a cushion member 12" according to a further alternative exemplary embodiment of the present invention. Cushion member 12", like cushion member 12', may be substituted for cushion member 12 in system 2 and used in connection with cushion pressure adjusting apparatus 60 and the methods of FIGS. 8 and 9. As seen in FIG. 14, cushion member 12" includes a number of the same components as cushion member 12, and like parts are labeled with like reference numerals. In particular, cushion member 12" includes a main body portion 34 as described elsewhere herein (FIG. 5), a frame member 128, and a self-sealing cap portion 36 coupled to frame member 128. Thus, cushion member 12" will include a plurality of chambers 48, with each chamber 48 having an individual membrane member 52 (formed by sealing cap portion 36) over it that seals the chamber 48.

Figure 15:
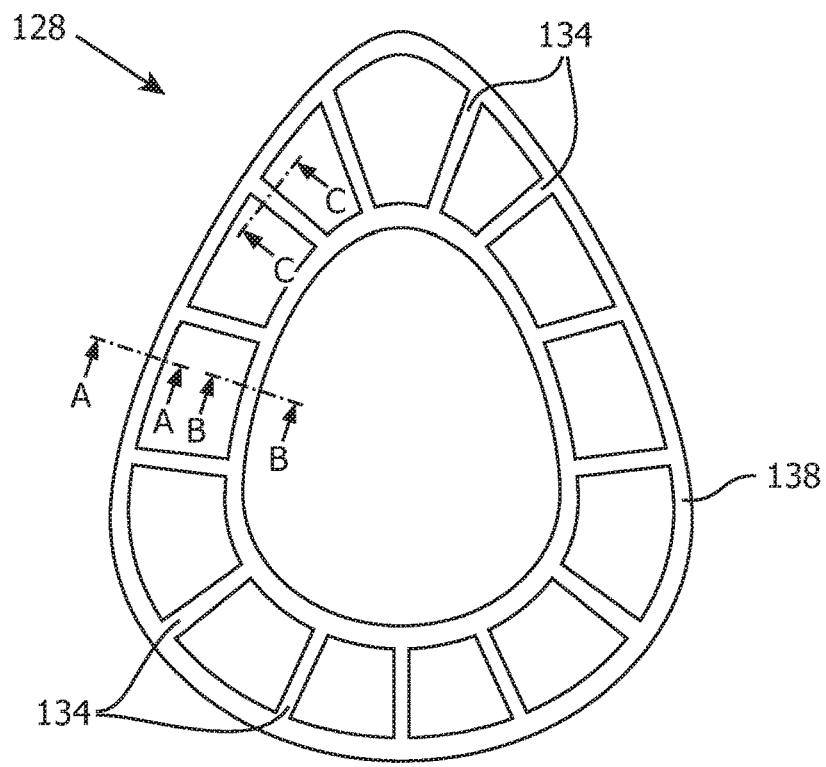
FIG. 15 is a front elevational view of a frame member of the cushion member of FIG. 14.
Figure 16:
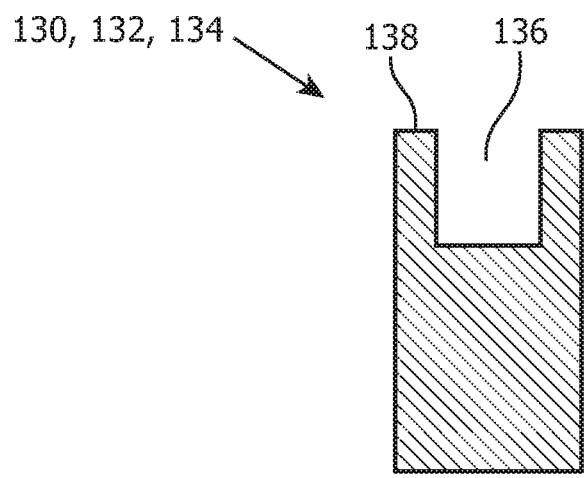
FIG. 16 is a cross-sectional view showing portions of the frame member of FIGS. 15.
Figure 17:
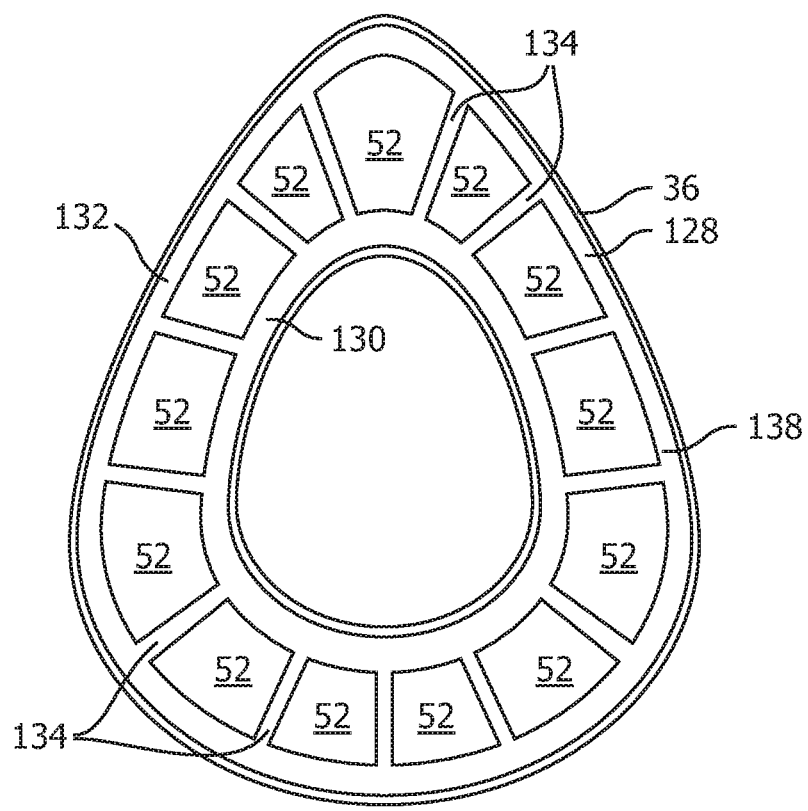
FIG. 17 is a front elevational view showing a structure resulting from a sealing cap member being overmolded onto the frame member of FIG. 15.

In the exemplary embodiment, cushion member 12" is made by first providing frame member 128 as shown in FIG. 15. Frame member 128 includes inner wall member 130, outer member 132, and a number of rib members 134 positioned around frame member 128 and each extending from inner wall member 130 to outer wall member 132. In the exemplary embodiment, frame member 128 is made of a rigid or semi-rigid material like polycarbonate or an injection molded thermoplastic. As seen in FIG. 16, which represents a cross-section of any one of inner wall member 130, outer member 132, or a rib member 134 (taken along lines A-A, B-B or C-C of FIG. 14, for example), in the exemplary embodiment, inner wall member 130, outer member 132, and rib members 134 each includes a portion of an inner groove 136 of frame member 128 (provided in a front surface 138 thereof). The function of inner groove 136 in this exemplary embodiment is described below. Self-sealing cap portion 36 is then overmolded on the rear surface of frame member 128 (opposite front surface 138) to form the frame structure 138 shown in FIG. 17. As seen in FIG. 17, this step results in the individual membrane members 52 being formed.

Next, to make cushion member 12", a main body portion 34 as shown in FIG. 5 is provided, and frame structure 138 is fixedly attached to main body portion 34. In particular, frame structure 138 is coupled to main body portion 34 in a manner wherein outer wall 38, inner wall 40 and each of the ribs 46 of main body portion 34 is received within inner groove 136 of frame member 128. In the exemplary embodiment, the two parts are held together by an adhesive provided in inner groove 136.

The concepts described in connection with FIGS. 1-17 are not limited to use with just sealing cushion members (e.g., mask cushions). Rather, such concepts may also be used to implement and custom fit other types of cushions that may be used in a patient interface device, such as, without limitation, forehand cushions/pads, cheek cushions/pads and chin cushions/pads.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device adjustment apparatus, comprising:
  a cushion support assembly having a support frame having a plurality of fluid delivery needles extending therefrom, the fluid delivery needles being spaced from one another along a perimeter of the support frame, the cushion support assembly being structured to hold a cushion member having a plurality of chambers, each of the chambers being covered by a self-sealing membrane member structured to self-seal after being punctured, wherein each of the fluid delivery needles is structured to puncture a respective one of the membrane members when the cushion member is held by the cushion support assembly such that each fluid delivery needle will be inserted through the respective one of the membrane members and into the chamber that the respective one of the membrane members covers; and a fluid delivery module structured to, for each respective one of the chambers, selectively (i) deliver fluid to the respective one of the chambers through the fluid delivery needle that is inserted into the respective one of the chambers when the cushion member is held by the cushion support assembly, and (ii) cause fluid present within the respective one of the chambers to be leaked out of the respective one of the chambers through the fluid delivery needle that is inserted into the respective one of the chambers when the cushion member is held by the cushion support assembly.

2. The patient interface device adjustment apparatus according to claim 1, wherein the fluid delivery needles comprise gas delivery needles, and wherein the fluid delivery module comprises a gas delivery module structured to, for each respective one of the chambers, selectively (i) deliver compressed gas to the respective one of the chambers through the gas delivery needle that is inserted into the respective one of the chambers when the cushion member is held by the cushion support assembly, and (ii) cause gas present within the respective one of the chambers to be leaked out of the respective one of the chambers through the gas delivery needle that is inserted into the respective one of the chambers when the cushion member is held by the cushion support assembly.

3. The patient interface device adjustment apparatus according to claim 2, wherein the gas delivery module comprises a source of gas structured to be selectively coupled to each of the gas delivery needles.

4. The patient interface device adjustment apparatus according to claim 3, wherein the source of gas comprises a tank of pressurized gas or a compressor.

5. The patient interface device adjustment apparatus according to claim 1, further comprising a pressure sensing module coupled to the fluid delivery needles, and a processing unit coupled to the pressure sensing module and the fluid delivery module, wherein the processing unit is programmed to control the fluid delivery module in a manner wherein the fluid delivery module will cause an internal pressure within each of the chambers to be substantially equal to a predetermined target pressure associated with the chamber when the cushion member is held by the cushion support assembly and when the cushion member is engaged by a face of a user.

6. The patient interface device adjustment apparatus according to claim 5, wherein the pressure sensing module comprises a plurality of pressure sensors, each of the pressure sensors being coupled to a respective one of the fluid delivery needles.

7. The patient interface device adjustment apparatus according to claim 5, wherein the pressure sensing module comprises a single pressure sensor structured to be selectively coupled to each of the fluid delivery needles.

8. The patient interface device adjustment apparatus according to claim 1, further comprising a processing unit coupled to the fluid delivery module, wherein the processing unit is programmed to control the fluid delivery module in a manner wherein the fluid delivery module will cause an internal pressure within each of the chambers to be set based upon input in the processing unit from a user when the cushion member is held by the cushion support assembly and when the cushion member is engaged by a face of the user.

9. The patient interface device adjustment apparatus according to claim 1, further comprising an chin support structured to engage a chin of a user and a forehead rest member structured to engage a forehead of the user when the cushion member is held by the cushion support assembly.

10. The patient interface device adjustment apparatus according to claim 9, wherein the chin support and the forehead rest member are adjustable.

11. The patient interface device adjustment apparatus according to claim 1, wherein the fluid delivery needles extend from a surface of the support frame provided in a first plane, and wherein the support frame is moveable in a direction that is perpendicular to the first plane.

12. A method of adjusting a cushion member having a plurality of chambers, each of the chambers being covered by a self-sealing membrane member structured to self-seal after being punctured, the method comprising:

holding the cushion member in a manner that provides access to each of the chambers through the self-sealing membrane member covering the chamber, wherein the holding comprises holding the cushion member with a cushion support assembly having a support frame having a plurality of fluid delivery needles extending therefrom in a manner wherein each fluid delivery needle punctures and is inserted through a respective one of the membrane members and into the chamber that the respective one of the membrane members covers, and wherein the fluid delivery needles are spaced from one another along a perimeter of the support frame; and adjusting an internal pressure within each respective one of the chambers through the self-sealing membrane member covering the respective one of the chambers when the cushion member is engaged by a face of a user, wherein the adjusting comprises, for each respective one of the chambers, at least one of: (i) delivering fluid to the respective one of the chambers through the fluid delivery needle that is inserted into the respective one of the chambers, and (ii) causing fluid present within the respective one of the chambers to be leaked out of the respective one of the chambers through the fluid delivery needle that is inserted into the respective one of the chambers.

13. The method according to claim 12, wherein the self-sealing membrane member is provided on a first side of the cushion member, and wherein the adjusting comprises adjusting the internal pressure within each of the chambers through the self-sealing membrane member covering the chamber when a second side of the cushion member opposite the first side of the cushion member is engaged by the face of the user.

14. The method according to claim 12, wherein the adjusting comprises causing the internal pressure within each of the chambers to be substantially equal to a predetermined target pressure associated with the chamber when the cushion member is engaged by the face of the user.

15. The method according to claim 12, wherein the predetermined target pressure associated with each chamber varies among the chambers.

16. The method according to claim 12, wherein the predetermined target pressure associated with each chamber is the same for each of the chambers.

17. The method according to claim 12, wherein the adjusting comprises causing the internal pressure within each of the chambers to be set to a level determined by the user when the cushion member is engaged by the face of the user.

18. The method according to claim 12, wherein the fluid delivery needles comprise gas delivery needles and the fluid comprises gas.

19. The method according to claim 12, further comprising removing the cushion member from the cushion support assembly such that each fluid delivery needle is removed from the respective one of the membrane members and in response thereto each of the membrane members self-seals.

* * * * *